(12) United States Patent
Hansmann et al.

(10) Patent No.: US 8,662,104 B2
(45) Date of Patent: Mar. 4, 2014

(54) SLOT VALVE FOR USE IN THE PNEUMATIC SWITCHING CIRCUIT OF A RESPIRATOR

(75) Inventors: Hans-Ulrich Hansmann, Barnitz (DE); Kirll Koulechov, Lübeck (DE); Tilman von Blumenthal, Lübeck (DE); Andreas Hengstenberg, Reinfeld (DE); Andreas Neumann, Klempau (DE); Torge Wall, Lübeck (DE); Andreas Otto, Bargteheide (DE); Markus Kaemer, Grönau (DE)

(73) Assignee: Dräger Medical GmbH, Lübeck (DE)

( * ) Notice: Subject to any disclaimer, the term of this patent is extended or adjusted under 35 U.S.C. 154(b) by 217 days.

(21) Appl. No.: 12/718,113

(22) Filed: Mar. 5, 2010

(65) Prior Publication Data
US 2010/0269829 A1 Oct. 28, 2010

(30) Foreign Application Priority Data
Apr. 28, 2009 (EP) ..................................... 09158904

(51) Int. Cl.
*F16K 17/26* (2006.01)
(52) U.S. Cl.
USPC ........ 137/493; 137/849; 137/859; 251/149.4; 251/149.5
(58) Field of Classification Search
USPC ........ 137/493, 849, 859; 128/203.11, 204.18, 128/204.21, 205.11; 251/149.4, 149.5
See application file for complete search history.

(56) References Cited

U.S. PATENT DOCUMENTS

| 2,003 | A | | 3/1841 | Osdel | |
|---|---|---|---|---|---|
| 966,137 | A | | 8/1910 | Storey | |
| 2,646,063 | A | * | 7/1953 | Hayes | ............................ 137/218 |
| 2,941,544 | A | * | 6/1960 | Peras | ............................ 137/844 |
| 3,856,262 | A | * | 12/1974 | Jordan | ............................ 251/340 |
| 4,351,328 | A | | 9/1982 | Bodai | |
| 4,416,473 | A | | 11/1983 | Lamy et al. | |
| 4,434,810 | A | * | 3/1984 | Atkinson | ........................ 137/493 |
| 4,557,261 | A | * | 12/1985 | Rugheimer | .................... 604/533 |
| 5,201,722 | A | * | 4/1993 | Moorehead et al. | ........... 604/247 |
| 5,775,325 | A | * | 7/1998 | Russo | ........................ 128/205.12 |
| 5,868,224 | A | * | 2/1999 | DiCarlo | ...................... 184/105.3 |
| 6,530,504 | B2 | * | 3/2003 | Socier | ............................ 222/494 |
| 7,766,044 | B2 | * | 8/2010 | Makowan et al. | ............ 137/849 |
| 2003/0189067 | A1 | | 10/2003 | Stull et al. | |
| 2004/0003846 | A1 | * | 1/2004 | Seidl | ............................ 137/493 |
| 2008/0029099 | A1 | * | 2/2008 | Storz | ........................ 128/205.24 |

FOREIGN PATENT DOCUMENTS

| DE | 32 04 110 C2 | 8/1983 |
|---|---|---|
| DE | 41 42 295 C2 | 7/1993 |
| DE | 198 38 370 C1 | 9/1999 |
| DE | 102005014650 | 8/2006 |
| EP | 0 474 069 A1 | 3/1992 |
| EP | 1 459 774 | 9/2004 |
| GB | 966137 | 8/1964 |

\* cited by examiner

*Primary Examiner* — Craig Schneider
*Assistant Examiner* — Jessica Cahill
(74) *Attorney, Agent, or Firm* — McGlew and Tuttle, P.C.

(57) ABSTRACT

A slot valve (20) for use in the pneumatic switching circuit of a respirator, wherein said slot valve is designed to act bidirectionally and to pass over into the opened state to make possible the flow of a fluid at different pressure threshold values depending on the direction of flow of a fluid.

19 Claims, 5 Drawing Sheets

SLOT VALVE FOR USE IN THE PNEUMATIC SWITCHING CIRCUIT OF A RESPIRATOR

CROSS REFERENCE TO RELATED APPLICATIONS

This application claims the benefit of priority under 35 U.S.C. §119 of European Patent Application EP 09 158 904.4 filed Apr. 28, 2009, the entire contents of which are incorporated herein by reference.

FIELD OF THE INVENTION

The invention relates to a slot valve for use in the pneumatic switching circuit of a respirator (also known as ventilator) and more particularly to a valve connected at a tube (e.g., an endotracheal tube or a tracheotomy cannula) coupled with the respirator.

BACKGROUND OF THE INVENTION

ARDS (acute respiratory deficiency syndrome) designates a sudden respiratory failure, which develops due to an acute inflammatory process of the lung tissue, in which the lungs extensively lose their ability to exchange gas. The permeability of the blood vessels in the pulmonary alveoli increases in ARDS and the pressure in the vessels drops, whereas it rises in other parts of the lung tissue. This leads to a life-threatening shortness of breath and to insufficient oxygen supply for the blood. The life-threatening hypoxia in the blood must be treated as quickly as possible by mechanically supporting breathing, i.e., artificial respiration with air enriched with oxygen. However, noninvasive respiration methods with merely increasing the oxygen concentration in the breathing air being supplied are often insufficient for the treatment of ARDS, because respirated ARDS patients have atelectatic (i.e., collapsed) lung areas, which can be opened (recruited) and made usable for gas exchange with a high respiration pressure only. However, the patient must be intubated for this, i.e., a tube (flexible tube) is pushed into the patient's trachea through the mouth or through the nose. The respiration is preferably carried out via an endotracheal tube or via a tracheotomy cannula. An endotracheal tube normally comprises a thin flexible tube, which is opened at both ends and whose lower end is pushed into the trachea. A cuff, which can be inflated via a thin flexible tube, which extends on the side of the tube, is located a short distance above the lower end. The trachea is sealed hereby. At the upper end, the endotracheal tube is equipped with a standardized connection piece, which makes possible connection to a respirator. A tracheotomy cannula is used in case of tracheotomy. The tracheotomy cannula also has an inflatable "block," which makes respiration possible and at the same time prevents pharyngeal secretion from entering the lungs downwards.

A residual pressure (PEEP=positive end-expiratory pressure) is preferably maintained at the end of expiration during the artificial respiration of ARDS patients. The pressure in the pulmonary alveoli is increased by the PEEP respiration, as a result of which the pulmonary alveoli are expanded, which leads to an enlargement of the area for the gas exchange and thus to an improvement of oxygen uptake. Furthermore, the risk of collapse of the pulmonary alveoli during expiration is reduced. The end-expiratory pressure in PEEP respiration frequently equals 10 mbar or higher in ARDS patients in order to prevent the lung areas opened with difficulty from recollapsing. It is necessary in most cases to artificially respirate an ARDS patient over several days or even weeks. However, some steps are necessary in the course of respiration in routine clinical practice, for example, suction of fluids from the lungs, repositioning of the patient, changing of the tube system, of the filter or of the respirator. The necessary pressure in the lungs cannot be continuously maintained during the performance of these clinically necessary steps, so that the damaged lung areas must be recruited time and time again.

U.S. Pat. No. 4,351,328 describes an adapter, which is designed to connect a respirator and an endotracheal tube. The adapter is provided, furthermore, with an opening, which is closed by means of a valve. The valve is designed as a slot valve and can be pierced by the suction tube when the latter is introduced into the opening from the outside.

U.S. Pat. No. 4,416,273 discloses a connection adapter for an endotracheal tube. The adapter has a port provided with a lamellar valve in order to make it possible to insert a suction catheter into the tube from the outside.

DE 32 04 110 C2 pertains to a tracheal tube for artificial respiration. The lower part of the tracheal tube is surrounded by a balloon cuff, which can be inflated via an inflating cannula to the extent that it comes into contact with the tracheal wall. A breathing tube connected to a respirator and a pressure-measuring cannula are provided in the interior space of the tracheal tube in order to make it possible to measure the pressure drop in the breathing tube or the intratracheal pressure.

DE 198 38 370 C1 describes a device for removing sputum from a tracheal catheter. The device has three openings, wherein a first opening is connected to the end of the catheter projecting from the trachea, a second opening can be coupled with an air filter for cleaning and sterilizing the air to be breathed in, and a third opening is connected to a collecting bag into which the sputum can flow. A spring-tensioned piston for closing the third opening is controlled by the breathing air during inspiration and expiration.

DE 41 42 295 C2 pertains to a valve for generating a control pressure in a pneumatic switching circuit. The valve has the embodiment of a circular closing element and has incisions, so that eight circle segments are formed, which can be bent up around the circumferential line of the closing segment. The extent of bending up changes depending on the pressure of the fluid acting on one side of the valve.

DE 10 2005 014 650 B3 discloses a connection piece with a distal end and a proximal end for connecting a tracheal tube and a respirator as well as with a branch for inserting a catheter. A valve made of material deformable elastically at least in some areas is provided in the branch, and said valve forms a beak section with a slot, which is opened during the insertion of the catheter. Closed suction systems, as they are shown in this document, prevent only the pressure during suction. Changing of the device and changing of the closed suction system itself, which is necessary at 48-hour intervals for hygienic reasons, continue to lead to collapse of the lungs and to a subsequent stressful recruitment maneuver.

None of the above-mentioned documents pertains to the respiration of ARDS patients, and none of these documents discloses respirators or respirating means in the pneumatic switching circuit between a respirator and a patient, which are designed to maintain a certain air pressure in the lungs of the patient to be respirated even when, for example, the respirator is being replaced.

SUMMARY OF THE INVENTION

The object of the present invention is therefore to make available a valve for use in the pneumatic switching circuit of a respirator, by means of which the above-mentioned drawbacks are overcome. In particular, it is the object of the present invention to make available a valve for use in or at a tube (e.g., an endotracheal tube or a tracheotomy cannula) coupled with the respirator, by means of which a pressure drop in the lungs of a patient (especially of an ARDS patient) can be effectively prevented from occurring.

These and other objects are accomplished by means of a slot valve having bidirectionally acting means for responding at different pressure threshold values depending on the direction of flow of a fluid.

An essential advantage of the slot valve according to the present invention is that the valve acts bidirectionally and responds independently from the direction of flow or the direction of action of a fluid at different threshold pressures.

Another advantage is that the slot valve according to the present invention is a self-closing valve and passes over into the opened state only when a threshold pressure is overcome in order to make it possible for a fluid to flow through. The quantity of fluid flowing through depends on the pressure of the fluid. Flow through the valve according to the present invention is possible from both directions (i.e., bidirectionally), and the threshold pressure that brings about opening of the slot valve differs depending on the direction of flow. The threshold pressure is preferably in a range of about 0 mbar to about 5 mbar in a first direction and in a range of about 5 mbar to about 15 mbar in a second direction. However, the exact value of these threshold values depends on the field of application of the valve and may also be, for example, in the range from markedly above 10 mar to a few 100 mbar.

The slot valve according to the present invention is preferably used in the pneumatic switching circuit of a respirator and is consequently arranged in the flow path between the respirator and the patient to be respirated, especially an ARDS patient, who is preferably respirated in the PEEP mode. The pressure drop in the patient's lungs to below a predetermined pressure level of, for example, between about 5 and 15 mbar can be prevented from occurring by means of the slot valve according to the present invention during disconnection at the endotracheal tube or at the tracheotomy cannula (when, for example, the respirator is being replaced). Furthermore, the valve is designed to make inspiration possible without the patient having to generate a high suctioning pressure for this. The threshold value for opening the valve in the suction direction is therefore preferably below 5 mbar. The necessary threshold pressure to open the valve must be higher in the direction of expiration and equals more than 5 mbar, preferably more than 10 mbar or in exceptional cases more than 15 mbar, and these values may also vary in an especially advantageous embodiment depending on the patient to be respirated, depending on the intensity of the ARDS and depending on other factors. Furthermore, the valve is designed to make it possible to suction fluids from the lungs by means of a special cannula. The slot valve according to the present invention has a hygienic design, which permits use for more than 1 week. In a preferred embodiment the valve is designed in a special manner in order not to hinder the flow of breath during normal respiration. The slot valve according to the present invention is provided for this purpose with means that can be actuated manually in order to make a changeover between different modes of operation possible in a simple manner.

The slot valve according to the present invention is formed by a membrane made of an elastic plastic or rubber in a preferred embodiment. The membrane preferably has a round basic shape, i.e., a circular contour line. Other shapes, for example, oval, rectangular or square shapes, are, of course, also conceivable, but the round shape is preferred because of the symmetry. A plurality of mutually intersecting slots, which fully extend through the membrane and thus form a plurality of circle segment-shaped lamellae, are provided in the middle of the membrane. For example, a total of four lamellae are formed by two slots intersecting each other at right angles, and six lamellae are formed by three slots, etc. Embodiments with more than six lamellae are possible as well.

The lamellae are closed, i.e., the slot surfaces of adjacent lamellae sealing abut against one another in the resting state (i.e., when there is essentially no pressure difference between the opposite sides of the membrane. According to a first embodiment, the membrane lamellae are located in an arched surface in their closed position. This arched surface may have, for example, the shape of a dome or of a spherical surface segment or correspond to the outer surface of a flat cone or of a flat pyramid. Regardless of the selected design, the lamellae are designed such that they open more easily in a first direction of flow than in a second direction when pressure (which acts, for example, via a fluid on the membrane lamellae) is applied. Consequently, no or only a low fluid pressure (first threshold pressure) is necessary in a first direction of flow to bend the lamellae from their closed position into their opened position (i.e., to open the valve), whereas a higher pressure (second threshold pressure) is necessary in the opposite, second direction of flow.

According to a second embodiment, the membrane lamellae are in an essentially planar plane in this closed state and are designed to bring about different threshold values to open the valve or the lamellae when pressure is being applied in different directions. This can be achieved by the thickness of the material of the lamellae being greater in an axial direction than the thickness of the material of the annular edge area or supporting ring of the valve membrane. It can be achieved hereby that the contact area of the slot surfaces is relatively large in the axial direction. However, the pivot lines of the lamellae which are present in the transition between the supporting ring and the lamellae are slightly offset at the same time in relation between the axial center of the radially extending contact areas between the lamellae, so that a higher pressure must be built up in an axial direction to pivot or fold over the lamellae from the closed position into the opened position. As an alternative, the thickness of the material of the lamellae may increase starting from the pivot lines of the lamellae in the radial direction towards the center of the valve membrane, whereby a similar effect is brought about. It is also possible to provide an annular groove on one side of the valve membrane. The "film hinges" for the membrane lamellae are formed by this groove, but the pivot lines of the hinges are shifted at the same time in the axial direction due to the provision of the annular groove. Consequently the threshold pressure for opening the valve is higher in one direction than in the opposite direction in this embodiment as well. The magnitude of the particular threshold values can be determined by the thickness of the membrane material, depth of the groove and elasticity of the membrane material. Furthermore, it is possible to provide the membrane lamellae with axially extending projections on one side directly at the slot surfaces abutting against each other between adjacent lamellae in order to thus enlarge the contact areas of the slots in the axial direction, as a result of which a relative axial displacement of the pivot lines of the lamellae is brought about at the same time.

The slot valve according to the present invention is suitable, for example, for being used in the breathing circuit for positive pressure respiration (e.g., PEEP) between a respirator and the patient. However, other applications, in which a similar valve function is desired, are conceivable as well.

The slot valve according to the present invention preferably has an essentially tubular valve housing with two ports generally located opposite each other and breathing gas can flow through it in two opposite direction. As was explained above, the slot valve according to the present invention has, in the flow channel between the two ports, a slotted membrane, which is fixed at its annular edge directly or indirectly in the housing and has membrane lamellae separated by incisions essentially radially in its center. According to a preferred embodiment, the membrane lamellae are arched at least partly such that when the valve is closed, the convex side of the arch points in the direction of the patient. During expiration, a moderate overpressure on the patient side against the convex arch at first leads to pressing of the arch along the radial partition lines (slots) between the membrane lamellae and hence to blocking of the flow channel. It is only when a predetermined threshold pressure of, for example, about 10 mbar is exceeded that this blocking force is overcome, the lamellae are folded over in the opposite direction (i.e., opposite the direction of the arching) and the flow channel is released for breathing gas to flow through. When the pressure again drops below the threshold pressure, the membrane lamellae fold back into their original arched position because of their own restoring forces and the flow channel is again blocked. By contrast, an overpressure on the opposite side (i.e., on the side of the respirator) against the concave underside of the arch leads to an immediate, nearly forceless flow of fluid in the direction of the patient during inspiration, because only a very low threshold value is necessary to open the lamellae.

The valve according to the present invention may be designed, furthermore, as a "pop-up" valve. A depressible or foldable, annular intermediate area is provided for this between the inner, circular slot area and the outer supporting ring. This intermediate area is folded up or into one another in the closed resting state of the valve or in the state that prevails when the patient is breathing in and only a low threshold value (overpressure on the side of the respirator) is necessary for opening the membrane lamellae. When the patient is breathing out (overpressure on the patient side), the folded-up intermediate area is first unfolded. If the pressure rises further and exceeds said threshold value (e.g., 10 mbar or more), the membrane lamellae are folded over as well. It was found that the membrane lamellae are pressed better against each other when the intermediate area is folded up and overpressure prevails on the patient side. It is only when the intermediate area is unfolded that the transition section between the membrane lamellae and the intermediate area acquires the necessary flexibility to make it possible for the membrane lamellae to fold over easily when the patient-side pressure exceeds the predetermined threshold value during expiration. The foldable intermediate area thus acts as a kind of securing means against premature folding over of the membrane lamellae under the threshold pressure.

A releasing means, which folds the membrane lamellae out of the closed position on actuation, so that the flow channel in the interior of the valve is released, is additionally provided in another advantageous embodiment of the present invention. In a preferred embodiment of the slot valve according to the present invention, the valve is inserted into the breathing circuit between an endotracheal tube or a tracheotomy cannula on one side (patient side) and the filter, artificial nose, closed suction system or Y-piece on the other side (respirator side). The valve has a housing, a slot membrane with, for example, four or six radially extending slots, as a result of which cut membrane lamellae are formed, a rotary ring and a spreader. The spreader can be pushed into the range of action of the slot membrane such that the membrane lamellae of the slot membrane permanently release the flow center and do not represent a relevant flow resistance. The spreader has two oblique holding noses, which open through the housing into a groove of the rotary ring, which said groove is designed as an oblique path. The rotary ring additionally has an annular groove, into which snaps a bead of the housing. As a result, the rotary ring is fixed against axial displacement at the housing. When rotating the rotary ring, the spreader is displaced axially over the two oblique paths and can thus be brought optionally into a position close to the Y-piece, where the spreader does not mesh with the membrane and a pressure drop in the patient's lungs below, for example, 10 mbar is avoided. The spreader meshes with the membrane lamellae in the opposite position near the patient and pushes same out of the flow center, whereby unhindered, bidirectional flow of fluid through the valve is made possible.

The present invention will now be described on the basis of an example with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
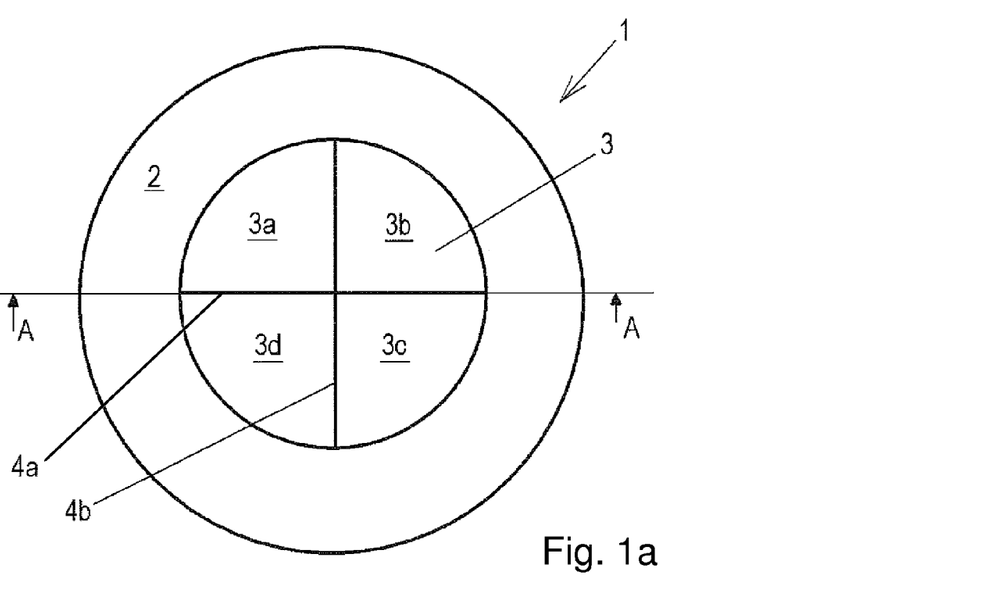
FIG. 1a is a schematic top view of an exemplary embodiment according to the present invention.

Referring to the drawings in particular, the figures will be described in detail below. FIG. 1a shows a top view of an exemplary slot membrane according to the present invention in its simplest embodiment. The slot membrane 1 has essentially the shape of a disk and is made of rubber, silicone rubber or a suitable elastic plastic material. The slot membrane 1 comprises a circular lamella area 3 with lamellae 3a through 3d, which are formed by slots 4a, 4b that intersect each other, and an annular supporting area 2, which surrounds the lamella area 3 and is used to fasten the slot membrane in a preferably annular valve housing. FIG. 1a shows two slots that intersect each other, as a result of which four circle segment-shaped lamellae are formed. However, it is also possible to provide three or more slots that intersect each other, as a result of which the total number of lamellae increases correspondingly.

Figure 1B:
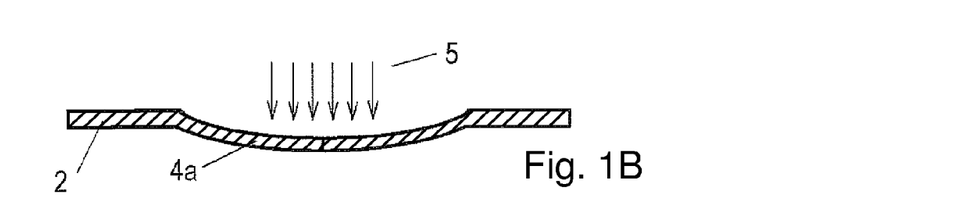
FIG. 1b is a cross-sectional view through line A-A from FIG. 1a, in which the arched lamella area is seen. The arrows indicate the direction of pressure in which a lower threshold value is necessary to open the valve.

FIG. 1b shows a cross-sectional view through line A-A from FIG. 1a, in which the arched lamella area 3 is seen along slot 4a. The membrane lamellae 3a-3d are in their closed position in an arched surface in this embodiment, which surface has the shape of a dome or a spherical surface segment in this case. However, the lamellae may also form the outer surface of a flat cone or of a flat pyramid. The lamellae are closed in the resting state being shown, and the slot surfaces of adjacent lamellae sealingly abut against one another. Arrows 5 show the direction of pressure of a fluid when an overpressure prevails on the side of a respirator (not shown), as it happens during inspiration by the patient. Only a low pressure threshold value is necessary here to fold the lamellae down to open the valve. A slight overpressure, which presses the downwardly pointing, convex arch of the lamellae and leads to the membrane lamellae being pressed mutually and hence to blocking of the flow channel, is at first generated during expiration (cf. FIG. 2c) by the patient on the patient side. It is only when a predetermined threshold pressure between about 5 mbar and 15 mbar is exceeded that this blocking force is overcome, the lamellae 3a-3d are folded upward and the flow channel is released. When the pressure again drops below the threshold pressure, the membrane lamellae fold back into their arched starting position because their own restoring forces and the flow channel is again blocked.

Figure 1C:
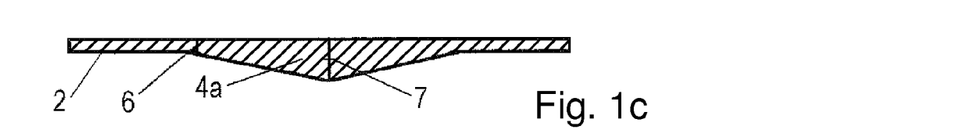
FIG. 1c is a cross-sectional view through line A-A from FIG. 1a, in which an alternative embodiment to FIG. 1b with varying material thickness of the membrane lamellae is seen.

FIG. 1c shows a cross-sectional view through line A-A from FIG. 1a, in which an alternative embodiment of the lamellae 3a-3d is seen. As is shown, the lamellae have a thickness increasing towards the center, as a result of which the contact surfaces between adjacent membrane lamellae rise in the axial direction in the area of the slots 4a, 4b. FIG. 1c shows that the material thickness of the lamellae asymmetrically increase in a radial direction starting from pivot sections of the lamellae toward the middle of the membrane to vary the different pressure thresholds. Since the pivot lines 6 of the lamellae are located above the center 7 of the contact surface in the axial direction in the figures, the lamellae can be pivoted downward with a low pressure, whereas a higher pressure is necessary to pivot the lamellae upward.

Figure 1D:
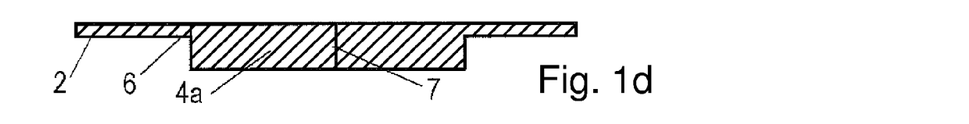
FIG. 1d is a cross-sectional view through line A-A from FIG. 1a, in which another alternative embodiment to FIG. 1c with constant material thickness of the membrane lamellae is seen, wherein the material thickness of the supporting ring is markedly smaller than that of the membrane lamellae.

FIG. 1d shows an alternative embodiment to FIG. 1c, in which the membrane lamellae 3a-3b have a constant material thickness, which is greater than the material thickness of the annular supporting area 2. Pivot line 6 of the lamellae is above the center 7 of the contact surface between the lamellae in the axial direction in this case as well. As a result, the lamellae can be pivoted downwards with a low pressure during inspiration, whereas a higher threshold pressure is needed to pivot the lamellae upwards.

Figure 1E:
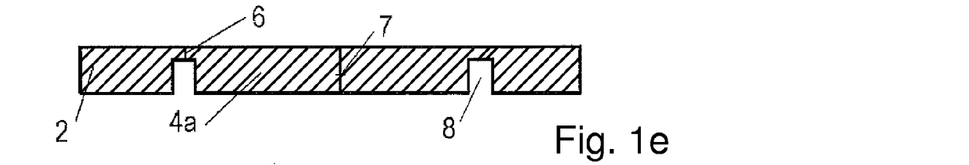
FIG. 1e is a cross-sectional view through line A-A from FIG. 1a, in which another alternative embodiment to FIG. 1d with constant material thickness of the entire membrane is seen, wherein an annular groove is provided between the supporting ring and the middle lamella area.

FIG. 1e shows a cross-sectional view through line A-A from FIG. 1a, in which an alternative embodiment to FIG. 1d with a constant material thickness of the entire slot membrane 1 is seen. An annular groove 8 is provided between the supporting ring 2 and the middle lamella area 3. The function of the different pressure threshold values in different directions of flow is embodied in this embodiment as well.

It is obvious that the slot membrane 1 from FIGS. 1a through 1e can be mounted into a preferably annular valve housing, wherein said supporting ring 2 can be inserted, for example, into an annular groove in the interior of the valve housing. Other modes of fastening, for example, bonding, welding, fusion, etc., are conceivable as well.

Figure 2A:
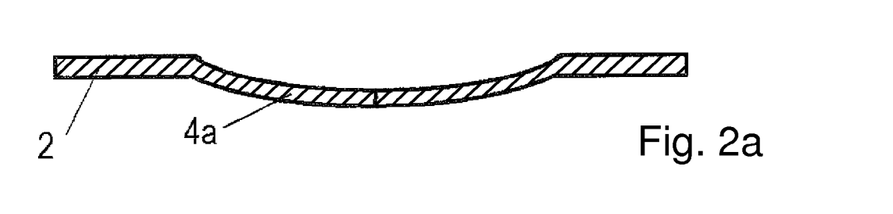
FIG. 2a is an embodiment of the slot membrane according to the present invention from FIG. 1b in the closed state.

FIG. 2a shows an embodiment of the slot membrane according to the present invention from FIG. 1b in the closed state. No pressure prevails on either side in the closed state or the pressures are below the threshold values on both sides.

Figure 2B:
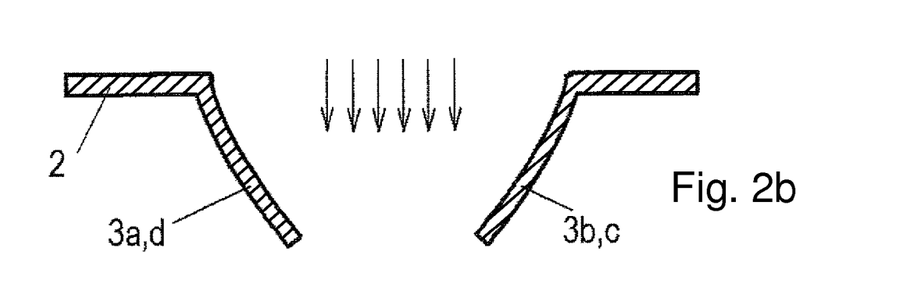
FIG. 2b shows the slot membrane from FIG. 2a in an opened state, wherein the pressure acts in the direction of inspiration and only a very low pressure is necessary to press the membrane lamellae downwards.

FIG. 2b shows the slot membrane from FIG. 2a in a downwardly opened state, wherein the pressure in the direction of inspiration is above a low predetermined threshold pressure of, for example, 0 to 5 mbar, which is necessary to push the membrane lamellae 3a-3d downwards.

Figure 2C:
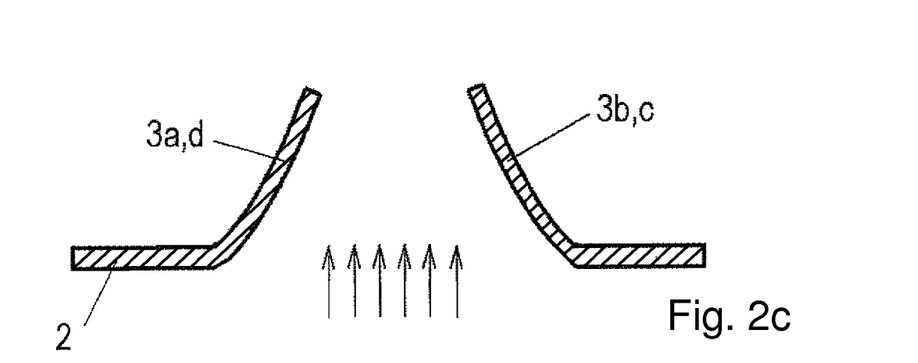
FIG. 2c shows the slot membrane from FIG. 2a in an opened state, wherein the pressure acts in the direction of expiration and a rather high pressure threshold value is necessary to fold over the membrane lamellae upwards.

FIG. 2c shows the slot membrane from FIG. 2a in an opened state, wherein the pressure acts in the direction of expiration. This pressure is above the threshold pressure of, for example, 10 or 15 mbar, which is necessary to push the membrane lamellae 3a-3d upwards.

Figure 3A:
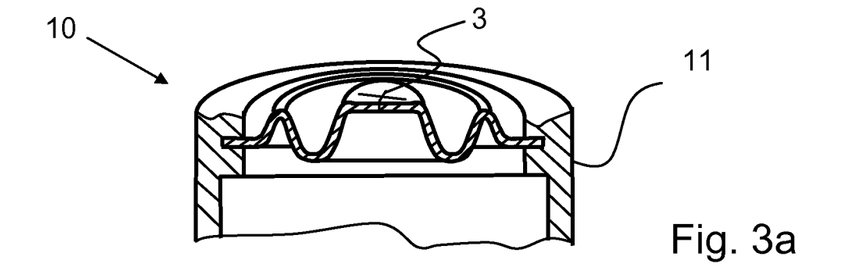
FIG. 3a is another preferred embodiment of the slot valve from FIGS. 1 and 2 in the closed state.
Figure 3B:
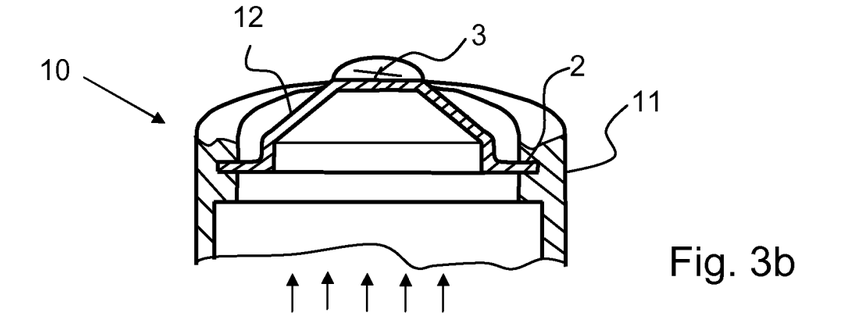
FIG. 3b shows the slot valve from FIG. 3a shortly before the opened state is reached in the direction of expiration.

FIG. 3a shows a preferred embodiment of the slot valve from FIGS. 1 and 2 in the closed state or shortly before the opened state is reached in the direction of inspiration (overpressure on the side of the respirator). Valve 10 preferably has an essentially tubular valve housing 11 with two generally opposite ports and breathing gas can flow through it in two opposite directions. Valve housing 11 may be designed to enable an adapter or a tube to be connected. A slot membrane 3, which is fastened to the valve housing at its annular supporting area 2, is provided between the two ports. The slot membrane 3 may have one of the embodiments shown in FIGS. 1 and 2. The valve 10 shown in FIGS. 3a through 3d is designed as a "pop-up" valve. A depressible or foldable, annular intermediate area 12, which may have different shapes, as this can best be seen in FIGS. 3a and 3d, is provided between the inner circular lamella area 3 and the outer supporting ring 2. As is shown in FIG. 3b, the intermediate area 12 is formed by an essentially conically tapering ring section, whereas the intermediate area 12 in FIG. 3d is designed as a cylindrical ring section, which is joined by a radially outwardly curved wall section, which is in turn connected to the supporting ring 2. FIG. 3a shows the closed resting state of the valve or the state that prevails when the patient is breathing in and only a low threshold value of, for example, less than 5 mbar (overpressure on the side of the respirator) is necessary for opening the membrane lamellae 3. When the pressure threshold value is exceeded, the lamellae 3a-3d would open in the downward direction, as this is shown in FIG. 2b. It is obvious that the lamella area 3 may have one of the configurations shown in FIGS. 1b through 1e.

Figure 3C:
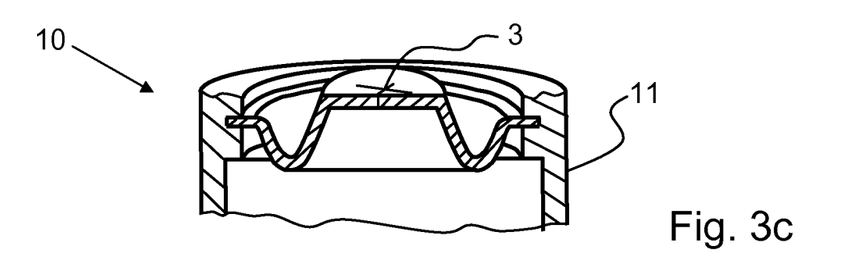
FIG. 3c is a variant of the slot valve from FIG. 3a in the closed state.
Figure 3D:
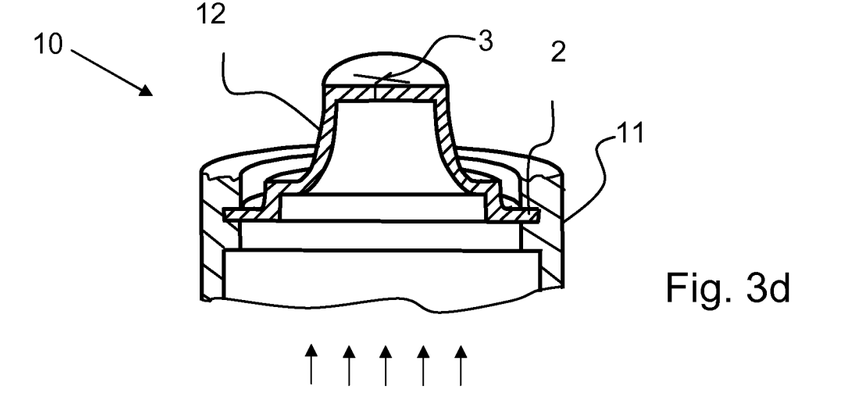
FIG. 3d shows the slot valve from FIG. 3c shortly before the opened state is reached in the direction of expiration.

As is shown in FIGS. 3a and 3c, the intermediate area 12 can be folded up or into one another. In this state the membrane lamellae 3a-3d are closed or folded downwards when the pressure threshold value is exceeded (overpressure on the side of the respirator=inspiration by the patient). When the patient stops breathing in, the lamellae are again closed because of their restoring force. When the patient begins to breath out, the lamellae are at first pressed against each other, whereby the lamellae are prevented from being folded over. Folding over is prevented, furthermore, by the folded-up intermediate area 12 applying a radially inwardly directed force to the lamellae. If the pressure continues to rise on the patient side, the intermediate area 12 is first unfolded, as is shown in FIGS. 3b and 3d. The force exerted by the intermediate area on the lamellae decreases in this state because it is only when the intermediate area is unfolded that the section between the membrane lamellae and the intermediate area acquires the necessary flexibility to make it possible for the membrane lamellae to fold over in the direction of expiration. Consequently, the lamellae are folded upward when the pressure threshold value is subsequently exceeded (for example, 10 or 15 mbar) on the patient side, as is shown in FIG. 2c. When the patient again stops breathing in, the pressure on the patient side will again drop below the above threshold value, and the lamellae will again return into their closed starting position because of their restoring force. The intermediate area is again folded up into the position shown in FIGS. 3a and 3c during the subsequent inspiration. The foldable intermediate area 12 thus acts as a kind of securing means against premature folding over of the lamellae below a defined pressure threshold value.

Figure 4:
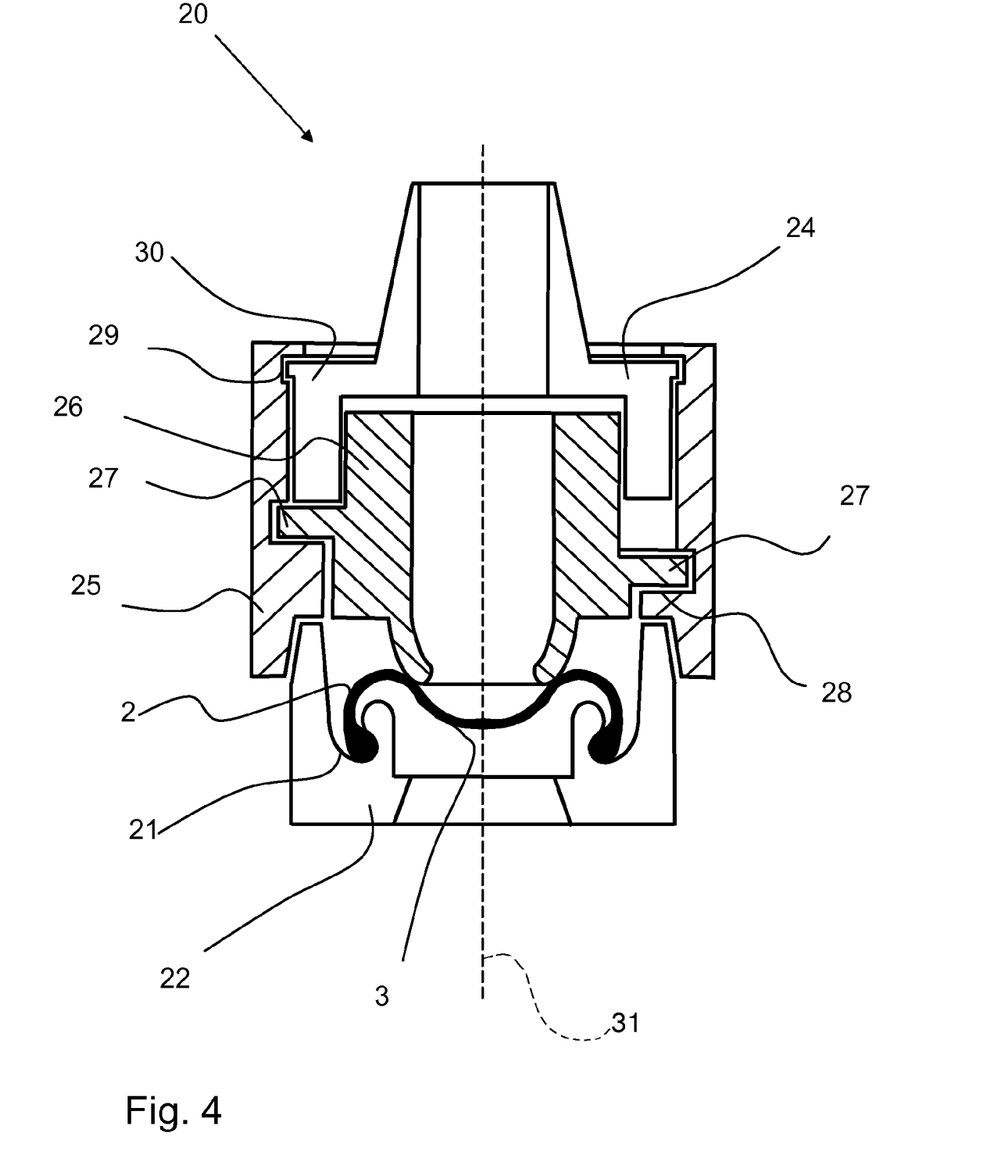
FIG. 4 is another embodiment of the slot valve according to the present invention, which is provided with a releasing means that can be actuated manually.
Figure 5:
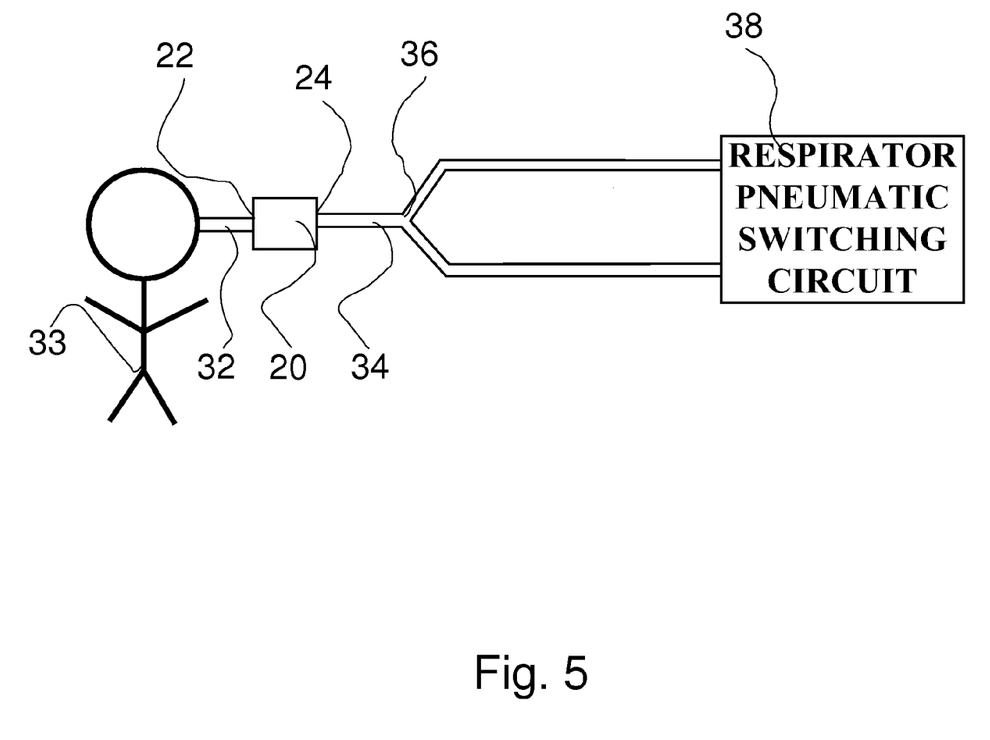
FIG. 5 is a schematic diagram of the valve in a respiration system.

FIG. 4 shows another embodiment of the slot valve according to the present invention, which is additionally provided with a releasing means. The slot valve 20 has a lamella area 3, in which a plurality of slotted lamellae 3a-3d are formed. The lamellae have a configuration similar to that in FIGS. 1b and 2a-2c. Only the extent of arching of the lamellae is greater in the embodiment according to FIG. 4. However, the lamellae may also have the configuration according to FIGS. 1c-1e. Furthermore, supporting ring 2 is bent downwardly/inwardly in a C-shaped manner in the direction of the arch in this embodiment in order to mesh with a correspondingly shaped recess 21 of a female breathing tube connector 22. The female breathing tube connector 22 is arranged on one end of the breathing tube 32 which can be an endotracheal tube or a tracheotomy cannula. The other end of the breathing tube 32 is adapted to being contact with the patient 33, as shown in FIG. 5. The female breathing tube connector 22 is connected in one piece to a male tube connector 24 to form the valve housing. The male tube connector 24 is equipped to be connected to an opening 34 of a Y-piece 36 and then to a respirator 38, also shown in FIG. 5. A closed suction device, whose suction cannula can pass axially through the slot membrane, is arranged for suctioning secretion between the Y-piece and the slot valve in an advantageous embodiment. Besides the housing formed by the female connector 22 and the male connector 24 and the slot membrane 1 with, for example, four or six radially extending slots, valve 20 has a rotary ring 25 held rotatably on housing 22, 24 and a spreader 26 mounted displaceably in the housing. The spreader 26 can be pushed into the range of action of the slot membrane 1 or of the lamella area 3 such that the membrane lamellae 3a-3d of the slot membrane are permanently opened in the direction of the patient in order to thus release the flow center in the interior of the valve and not to represent a relevant flow resistance.

Spreader 26 has two holding noses 27, which open through the housing (between the male and female tube connectors 22, 24) into the oblique path 28 of the rotary ring 25. The rotary ring 25 has, besides the oblique path 28, an annular groove 29, into which snaps a bead 30 of the housing. The rotary ring 25 is axially fixed at the housing hereby. When rotating the rotary ring, spreader 26 is axially displaced over the oblique path 28 and can thus be brought optionally into a position close to the Y-piece (respirator side), where the spreader does not mesh with the membrane lamellae and a pressure drop in the patient's lungs below, for example, 10 mbar is thus avoided. In the opposite position near the patient the spreader meshes with the membrane lamellae and pushes these out of the flow center, as a result of which bidirectional flow of fluid through the slot valve 20 is made possible.

While specific embodiments of the invention have been described in detail to illustrate the application of the principles of the invention, it will be understood that the invention may be embodied otherwise without departing from such principles.

What is claimed is:

1. A respiration system for a patient, the respiration system comprising:
a breathing tube bidirectionally conveying a flow of fluid to a patient, said breathing tube having diametrically opposite first and second ends, said first end of said breathing tube being adapted to be in contact with the patient;
a slot valve arranged at said second end of said breathing tube, said slot valve opening in a first direction of flow toward the patient when a pressure in said first direction of flow is above a first pressure threshold, said slot valve closing in said first direction of flow when said pressure in said first direction of flow is below said first pressure threshold, said slot valve opening in a second direction of flow away from the patient when a pressure in said second direction of flow is above a second pressure threshold, said slot valve closing in said second direction of flow when said pressure in said second direction of flow is below said second pressure threshold, said second pressure threshold being higher than said first pressure threshold, said slot valve including a membrane defining a plurality of slots which intersect each other and extend completely through said membrane, said slots forming a plurality of lamellae that are pivotal about pivot lines, said lamellae contact each other to close said valve, a material thickness of said lamellae asymmetrically varying as a function of a radial position of the membrane, said material thickness varying asymmetrically to vary a value of said first and second pressure thresholds.

2. A respirator system in accordance with claim 1, wherein:
said membrane includes a support area around said lamella, said lamella being pivotally connected to said support area about said pivot lines;
edges of said lamellae contact each other at said slot to close said valve, a material thickness of said lamellae at said edges being greater than a material thickness at said pivot lines to vary a value of said first and second pressure thresholds; and
said pivot sections are arranged axially offset from a center of said material thickness of said lamella at said edges to open said slot valve from said closed position at said different pressure threshold values.

3. A respirator system with a pneumatic switching circuit the respirator system comprising:
a breathing tube bidirectionally conveying a flow of fluid to a patient, said breathing tube having diametrically opposite first and second ends, the first end of the breathing tube being adapted to be in contact with the patient;

a slot valve connected to said second end of said breathing tube, said slot valve opening from a closed position when fluid in said breathing tube is above different pressure threshold values depending on the direction of flow of a fluid, said slot valve including a membrane with a center lamella area, said lamella area of said membrane defining a plurality of intersecting slots forming a plurality of lamellae, said lamellae being constructed to be easier to open upon application of pressure in a first direction than in a second direction; wherein the material thickness of the lamellae asymmetrically increases in a radial direction starting from pivot sections of the lamellae towards the middle of the membrane to vary the different pressure threshold values;

a valve housing wherein said membrane is inserted into the valve housing, wherein the membrane is limited at its outer edge by a supporting ring, the membrane comprising an elastic plastic or rubber, a material thickness of the lamellae is greater in an axial direction than a material thickness of the supporting ring of the membrane.

4. A respirator system in accordance with claim 3, wherein said slot valve has an open state and a closed state to provide a self-closing valve that passes over into the opened state to make possible the flow of a fluid only when pressure threshold values are exceeded, the pressure threshold values differing depending on the direction of flow of a fluid.

5. A respirator system in accordance with claim 3, wherein the threshold pressure values comprise a range of 0 mbar to 5 mbar in a first direction and a range of 5 mbar to 15 mbar in a second direction.

6. A respirator system in accordance with claim 1, wherein the membrane has a round, oval, rectangular or square basic shape.

7. A respirator system in accordance with claim 3, wherein slot surfaces of adjacent lamellae sealingly abut against each other in the closed position when the fluid is below the respective pressure threshold value.

8. A respirator system in accordance with claim 3, wherein the lamella area of the membrane provided with slots forms an arched surface, wherein said arched surface has a dome shape or a spherical surface segment, or said arched surface corresponds to the outer surface of a flat cone or of a flat pyramid.

9. A respirator system in accordance with claim 3, wherein the asymmetrical thickness of said lamellae cause said lamellae to bend more easily in a first direction than in a second direction when pressure is applied.

10. A respirator system in accordance with claim 3, further comprising a flow channel between two ports wherein said membrane is fixed at an annular edge directly or indirectly in a flow channel housing and said lamellae are arched at least partially, in a middle.

11. A respirator system in accordance with claim 3, wherein a depressible or foldable, annular intermediate area is provided between an inner, circular slot area of the membrane and the outer supporting ring, said intermediate area folding and unfolding between a folded state and unfold state dependent upon a pressure across said slot valve, said folded state of said intermediate area applying a radially inwardly directed force to said lamella, said unfolded state decreasing said radially inwardly directed force.

12. A respirator system in accordance with claim 3, wherein:
edges of said lamellae contact each other at said slot to close said valve, a material thickness of said lamellae at said edges being greater than a material thickness at said pivot lines to vary a value of said first and second pressure thresholds;

said lamella is pivotally connected to said support ring about said pivot sections; and said pivot sections being arranged axially offset from a center of said thickness of said lamella at said slots to open said slot valve from said closed position at said different pressure threshold values.

13. A respirator system in accordance with claim 3, further comprising releasing means for folding the membrane lamellae out of the closed position on actuation, so that a flow channel in an interior of the valve is released.

14. A respirator system in accordance with claim 13, further comprising:
a valve housing holding the slot valve;
said slots being a plurality of radially extending slots forming the plurality of membrane lamellae; and
a rotary ring connected to said valve housing, said rotary ring defining an oblique path, wherein said releasing means is a spreader, wherein said spreader is pushed into the range of action of the membrane such that the lamellae of the membrane release a flow center and provide a lower flow resistance, wherein said spreader has two holding noses, which engage with the oblique path of the rotary ring, as a result of which the spreader is displaced axially during rotation of the rotary ring.

15. A respirator system in accordance with claim 14, wherein the rotary ring has an annular groove, into which snaps a bead of the housing, as a result of which the rotary ring is fixed to the housing against axial displacement.

16. A respiration system for a patient, the respiration system comprising:
a breathing tube bidirectionally conveying a flow of fluid to a patient, said breathing tube having diametrically opposite first and second ends, said first end of said breathing tube being adapted to be in contact with the patient;

a slot valve arranged at said second end of said breathing tube, said slot valve opening in a first direction of flow toward the patient when a pressure in said first direction of flow is above a first pressure threshold, said slot valve closing in said first direction of flow when said pressure in said first direction of flow is below said first pressure threshold, said slot valve opening in a second direction of flow away from the patient when a pressure in said second direction of flow is above a second pressure threshold, said slot valve closing in said second direction of flow when said pressure in said second direction of flow is below said second pressure threshold, said second pressure threshold being higher than said first pressure threshold, said slot valve including a membrane defining a plurality of slots which intersect each other and extend completely through the membrane, said slots forming a plurality of lamellae that are pivotal about pivot lines and contact each other to close said valve, a material thickness of said membrane being greater adjacent said slot than at said pivot lines to vary a value of said first and second pressure thresholds;

a valve housing arranged around said slot valve, said membrane being connected to said valve housing;

a spreader movably arranged in said valve housing between a first and second position, said first position of said spreader allowing said slot valve to operate according to said first and second pressure thresholds, said material thickness of said membrane solely varies a value of said first and second pressure thresholds in said first position of said spreader, said second position of said spreader folding the membrane lamellae about said pivot lines and out of contact with each other to open said slots and said slot valve, said second position of said spreader being arranged to remove said first and second pressure thresholds, said spreader defining a central flow passage conveying the flow of fluid to the patient, said central passage being in communication with the open slots and said breathing tube when said spreader is in said second position.

17. A respiration system in accordance with claim 16, wherein:
   said breathing tube is one of an endotracheal tube or a tracheotomy cannula.

18. A respiration system in accordance with claim 16, further comprising:
   one of a Y-piece and a respirator connected to said slot valve on a side of said slot valve diametrically opposite said second end of said breathing tube.

19. A respiration system in accordance with claim 16, wherein:
   a material thickness of said lamellae asymmetrically varying as a function of a radial position starting from the pivot lines thereof towards a middle of the membrane, said material thickness varying asymmetrically to vary a value of said first and second pressure thresholds.

* * * * *